United States Patent [19]

Hardy et al.

[11] 3,957,809

[45] May 18, 1976

[54] CERTAIN 2-ALKYL-5-OXYMETHYLTHIAZOLES

[75] Inventors: Michel Hardy, Maisons-Alfort; Daniel Humbert, Paris, both of France

[73] Assignee: Roussel-UCLAF, Paris, France

[22] Filed: Aug. 8, 1974

[21] Appl. No.: 495,556

[30] Foreign Application Priority Data

Aug. 29, 1973 France .................. 73.31182

[52] U.S. Cl. .................. 260/302 R; 424/270
[51] Int. Cl.² ..................... C07D 277/24
[58] Field of Search .................. 260/302 R

[56] References Cited
UNITED STATES PATENTS 3,299,083  1/1967  Kollonitsch .............. 260/302 R
3,390,188  6/1968  Chamberlin et al. ........ 260/302 R

*Primary Examiner*—R. Gallagher
*Attorney, Agent, or Firm*—Hammond & Littell

[57] ABSTRACT

Novel thiazole derivatives of the formula

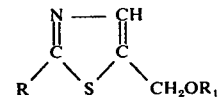

I wherein R is alkyl of 2 to 12 carbon atoms and $R_1$ is selected from the group consisting of hydrogen, alkyl of 1 to 8 carbon atoms and acyl of an organic carboxylic acid of 1 to 12 carbon atoms having hypolipemiant activity with a very prolonged vasodilatatory activity and their preparation.

4 Claims, No Drawings

CERTAIN 2-ALKYL-5-OXYMETHYLTHIAZOLES

STATE OF THE ART

Zubarovskii et al [Chem. Ab., Vol 58 (1963), p. 2,525b] describes the preparation of 2-methyl-thiazole-5-methanol by reaction of ethyl 2-methyl-thiazole-5-carboxylate with lithium aluminum hydride but does not describe any pharmacological properties therefor.

OBJECTS OF THE INVENTION

It is an object of the invention to provide the novel thiazole derivatives of formula I and a process for their preparation.

It is another object of the invention to provide novel hypolipemiant and vasodilatatory compositions.

It is a further object of the invention to provide a novel method of inducing hypolipemic and vasodilatatory activity in warm-blooded animals.

These and other objects and advantages of the invention will become obvious from the following detailed description.

THE INVENTION

The novel thiazole derivatives of the invention are compounds of the formula

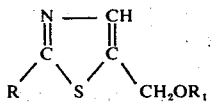

wherein R is alkyl of 2 to 12 carbon atoms and $R_1$ is selected from the group consisting of hydrogen, alkyl of 1 to 8 carbon atoms and acyl of an organic carboxylic acid of 1 to 12 carbon atoms.

Among the preferred compounds of formula I are those where R is a linear alkyl such as ethyl, n-propyl, n-butyl, n-pentyl, n-hexyl or n-undecyl; and $R_1$ is hydrogen, alkyl of 1 to 4 carbon atoms such as methyl, ethyl, propyl, isopropyl, butyl, isobutyl, or tert.-butyl or acyl of a saturated or unsaturated aliphatic acid, particularly alkanoic acids such as formic acid, acetic acid, propionic acid, butyric acid, isobutyric acid or undecylic acid; cycloalkylcarboxylic acids or cycloalkylalkanoic acids such as cyclopropylcarboxylic acid, cyclopentylcarboxylic acid, cyclohexylcarboxylic acid, cyclopentylacetic acid, cyclohexylacetic acid, cyclopentylpropionic acid or cyclohexylpropionic acid; benzoic acid or phenylalkanoic acids such as phenylacetic acid or phenylpropionic acid.

The most preferred compounds of the invention are 2-ethyl-thiazole-5-methanol, 2-propyl-thiazole-5-methanol and 2-hexyl-thiazole-5-methanol.

The novel process of the invention for the preparation of compounds of formula I in which $R_1$ is hydrogen comprises reacting a compound of the formula

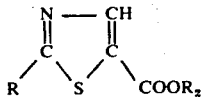

wherein R has the above definition and $R_2$ is hydrogen or alkyl of 1 to 8 carbon atoms with a reducing agent to form the corresponding compound of formula I in which $R_1$ is hydrogen. The latter may be reacted with an etherification agent or an esterification agent to form the compounds of formula I wherein $R_1$ is alkyl of 1 to 8 carbon atoms or acyl of an organic carboxylic acid of 1 to 12 carbon atoms.

Preferably, $R_2$ is alkyl of 1 to 4 carbon atoms. The reducing agent is preferably a mixed hydride such as lithium aluminum hydride or lithium borohydride. The reduction may also be effected with sodium in the presence of an alkanol such as methanol or ethanol. The reduction may be effected in one or more organic solvents, preferably an ether such as dioxane, ethyl ether or tetrahydrofuran. The preferred mode of the invention comprises using lithium aluminum hydride in tetrahydrofuran.

The etherification reaction is preferably effected with an alkyl halide such as an alkyl iodide or chloride in the presence of a basic agent such as sodium or sodium hydride. The reaction may also be effected by reacting alkyl sulfates, sulfonates or sulfites with alkali metal alcoholates of the compounds of formula I wherein $R_1$ is hydrogen. The reaction may also be a dehydration of the alcohol of formula I with an alcohol in the presence of sulfuric acid.

The esterification of the alcohols of formula I is preferably obtained by reaction with the acid or a functional derivative thereof such as the acid anhydride or an acid halide, preferably the acid chloride or bromide.

The starting compounds of formula II may be prepared by the process described in French Pat. No. 2,047,876.

The novel hypolipemiant and vasodilatatory compositions of the invention are comprised of an effective amount of at least one thiazole of formula I and a pharmaceutical carrier. The concentration of the active ingredient may be 5 to 95%, preferably 10 to 50%, by weight of the composition. The composition may be in the form of tablets, coated tablets, cachets, capsules, granules, emulsions, drops, syrups, suppositories or injectable solutions or suspensions.

The compositions have a marked hypolipemiant activity and a very prolonged vasolidatatory activity and therefore are useful for the treatment of hyperlipidemia, of coronary insufficencies, cardiac insufficencies of atheromatosis origin, of chronic anginic states and of functional troubles of hypertension.

The novel method of the invention for inducing hypolipemic and vasolidatatory activity in warm-blooded animals comprises administering to warm-blooded animals an effective amount of at least one thiazole of formula I. The product may be administered orally, rectally or transcutaneously. The usual daily dose is 10 to 50 mg/kg.

In the following examples there are described several preferred embodiments to illustrate the invention. However, it should be understood that the invention is not intended to be limited to the specific embodiments.

EXAMPLE 1

2-ethyl-thiazole-5-methanol

STEP A: methyl 2-ethyl-thiazole-5-carboxylate

A solution of diazomethane in methylene chloride was added to a suspension of 10.45 g of 2-ethyl-thiazole-5-carboxylic acid in 30 ml of methylene chloride until efferversence stopped and the methylene chloride was distilled. The oily residue was chromatographed over silica and was eluted with a 1:1 mixture of benzene-ethyl acetate to obtain 11.3g of methyl 2-ethyl-thiazole-5-carboxylate.

STEP B: 2-ethyl-thiazole-5-methanol 2.4 g of mixed lithium aluminum hydride was added under nitrogen to a solution of 11.3 g of methyl 2-ethylthiazole-5-carboxylate in 100 ml of anhydrous tetrahydrofuran at 20° to 25°C and the mixture was refluxed for 1½ hours. After cooling the mixture, excess lithium aluminum hydride was destroyed by the addition of ethyl acetate. The mixture was added to water and was vacuum filtered. The recovered precipitate was empasted with ethyl acetate and then with a methanol methylene chloride mixture. The filtrate was washed with water, dried and evaporated to dryness to obtain 9.5 g of an oil which was rectified under reduced pressure to obtain 10.4 g of 2-ethyl-thiazole-5-methanol with a boiling point of 78°C at 0.1 mmHg.

EXAMPLE 2

2-propyl-thiazole-5-methanol

STEP A: ethyl 2-propyl-thiazole-5-carboxylate

A current of hydrochloric acid gas was passed with stirring through a solution of 30 g of 2-propyl-thiazole-5-carboxylic acid in 400 ml of absolute ethanol overnight and the ethanol was then evaporated off. The oily residue was taken up in ether containing 10% of potassium carbonate and the mixture was extracted with ether. The ether extracts were washed with water until a pH of 6 was obtained and the resulting yellow oil was purified by distillation to obtain 31.2 g of ethyl 2-propyl-thiazole-5-carboxylate with a boiling point of 139°–140°C at 16 mmHg.

STEP B: 2-propyl-thiazole-5-methanol 5.8 g of mixed lithium aluminum hydride were added with stirring under a nitrogen atmosphere to 150 ml of anhydrous ether and a solution of 15.1 g of ethyl 2-propyl-thiazole-5-carboxylate in 30 ml of anhydrous ether was added thereto dropwise. The mixture was stirred for 2 hours, cooled and then 20 ml of ethyl acetate followed by 20 ml of water were added. The organic phase was decanted after filtering off the precipitate formed and the ether phase was dried over magnesium sulfate and evaporated to dryness under reduced pressure. The residue was distilled to obtain 6.2 g of 2-propyl-thiazole-5-methanol with a boiling point of 86°C at 0.01 mmHg. The product could be used to fill capsules with 500 mg of the said product and sufficient polyoxyethyleneglycol to fill the capsules.

EXAMPLE 3

2-hexyl-thiazole-5-methanol

Using the procedure of Example 1, ethyl 2-hexyl-thiazole-5-carboxylate (prepared by method of French Pat. No. 2,047,876) was reacted to obtain 2-hexyl-thiazole-5-methanol with a boiling point of 130°C at 0.2 mmHg.

PHARMACOLOGICAL STUDY OF 2-PROPYL-THIAZOLE-5-METHANOL

A. Acute toxicity

The acute toxicity of the product of the invention was determined on lots of 10 mice weighing between 18 and 22 g and the product was administered intraperitoneally. The product was administered intraperitoneally at increasing doses in suspension in aqueous gum. The animals were kept under observation for a week and the average lethal dose ($DL_{50}$) was graphically determined by the method of Dragstedt and Lang and it was about 1000 mg/kg.

B. Hypolipemiant Activity

The hypolipemiant activity was determined by the technique of Jacobs et al [Proc. Soc. Exp. Biol. Med., Vol. 119 (4) (1965), p. 1117-1120] using male rats of the Wistar strain weighing 160 to 180 g. The animals were starved for 24 hours and then were administered by an esophagus probe a 5% suspension of the product in gum water at doses of 2, 5, 10 and 20 mg/kg. 4 hours after ingestion of the product, samples of the blood were used to determined the amount of triglycerides therein.

This was determined by extracting the seric lipids with petroleum ether in the presence of ethanol, and submitting the lipidic solution to several treatments with 87% ethanol to obtain a solution the upper part of with contains the glycerides and the lower part, the phospholipids. The ratio of the glycerides was determined by dosage of the glycerol, periodic oxidation and dosage of formaldehyde by chromotropic acid. The results are reported in the following Table.

| Dose in mg/kg | % lessening as compared to controls |
|---|---|
| 2 | 25 |
| 5 | 57 |
| 10 | 55 |
| 20 | 66 |

The results of the Table show that the product is very clearly active against blood lipids.

C. Peripheric vasodilatatory Activity

The peripheric vasodilatatory effect was determined on non-pigmented ears rabbit and was manifested by the appearance of a reddening of the ears. The animals were not fed and the product was orally administered at different doses to determine the time of the reddening appearance of the ears and the duration and intensity of the reddening was noted on a scale of 0 to +++. The results are reported in the following Table.

| Dose in mg/kg | Latency | Duration | Intensity |
|---|---|---|---|
| 25 | 20 min. | 40 min. | +++ |
| 50 | 18 min. | 55 min. | +++ |
| 50-nicotinic Acid | 4 min. | 25 min. | +++ |

The product has a clear peripheric vasodilatatory activity in this test.

Various modifications of the compositions and methods of the invention may be made without departing from the spirit or scope thereof and it is to be understood that the invention is intended to be limited only as defined in the appended claims.

We claim:

1. A compound of the formula

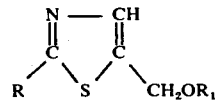

wherein R is alkyl of 2 to 12 carbon atoms and $R_1$ is selected from the group consisting of hydrogen, alkyl of 1 to 8 carbon atoms and acyl of an organic carboxylic acid of 1 to 12 carbon atoms selected from the group consisting of alkanoic acids, cycloalkylcarboxylic acids, cycloalkylalkanoic acids, benzoic acid, and phenyl alkanoic acids.

2. A compound of claim 1 which is 2-ethyl-thiazole-5-methanol.

3. A compound of claim 1 which is 2-propyl-thiazole-5-methanol.

4. A compound of claim 1 which is 2-hexyl-thiazole-5-methanol.

* * * * *